(12) United States Patent
Samejima et al.

(10) Patent No.: US 10,501,663 B2
(45) Date of Patent: Dec. 10, 2019

(54) BASE POLYMER FOR HOT MELT ADHESIVE

(71) Applicant: IDEMITSU KOSAN CO., LTD., Chiyoda-ku (JP)

(72) Inventors: Kanako Samejima, Funabashi (JP); Harumi Nakashima, Sodegaura (JP); Yutaka Minami, Chiba (JP); Tomoaki Takebe, Chiba (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 18 days.

(21) Appl. No.: 15/537,142

(22) PCT Filed: Dec. 22, 2015

(86) PCT No.: PCT/JP2015/085890
§ 371 (c)(1),
(2) Date: Jun. 16, 2017

(87) PCT Pub. No.: WO2016/104539
PCT Pub. Date: Jun. 30, 2016

(65) Prior Publication Data
US 2018/0265752 A1     Sep. 20, 2018

(30) Foreign Application Priority Data

Dec. 22, 2014  (JP) ................... 2014-259409

(51) Int. Cl.
| | | |
|---|---|---|
| *C09J 123/14* | (2006.01) | |
| *C09J 11/06* | (2006.01) | |
| *C09J 5/00* | (2006.01) | |
| *C09J 123/08* | (2006.01) | |

(52) U.S. Cl.
CPC ............ *C09J 123/14* (2013.01); *C09J 5/00* (2013.01); *C09J 11/06* (2013.01); *C09J 123/0815* (2013.01); *C09J 2423/04* (2013.01); *C09J 2423/10* (2013.01)

(58) Field of Classification Search
None
See application file for complete search history.

(56) References Cited

U.S. PATENT DOCUMENTS

2006/0020067 A1* 1/2006 Brant ............... C09J 123/10
524/236
2010/0305531 A1  12/2010  Bach et al.
2011/0076905 A1   3/2011  Muessig et al.
2011/0172348 A1*  7/2011  Hoya ............... C08L 23/142
524/528
2014/0199545 A1   7/2014  Moriguchi et al.
2014/0199908 A1   7/2014  Inoue
2015/0284600 A1  10/2015  Kobayashi et al.
2015/0368522 A1  12/2015  Fujinami et al.

FOREIGN PATENT DOCUMENTS

| JP | 2010-506983 A | 3/2010 |
|---|---|---|
| JP | 2011-524919 A | 9/2011 |
| JP | 2013-64055 A | 4/2013 |
| JP | 2013-64056 A | 4/2013 |
| WO | 03/091289 A1 | 11/2003 |
| WO | 2010/032600 A1 | 3/2010 |
| WO | 2014/077258 A1 | 5/2014 |
| WO | 2014/129301 A1 | 8/2014 |
| WO | 2014/192767 A1 | 12/2014 |

OTHER PUBLICATIONS

Combined Office Action and Search Report dated Sep. 21, 2018 in Chinese Patent Application No. 201580069362.9 (with English translation of categories of cited documents), 8 pages.
International Search Report dated Mar. 29, 2016, in PCT/JP2015/085890, filed Dec. 22, 2015.
Combined Chinese Office Action and Search Report dated Jul. 19, 2019 in Chinese Patent Application No. 201580069362.9, 8 pages.
Office Acton as received in the corresponding Japanese Patent Application No. 2016-566411 dated Aug. 13, 2019 w/English Translation.

* cited by examiner

*Primary Examiner* — Christopher M Rodd
(74) *Attorney, Agent, or Firm* — Oblon, McClelland, Maier & Neustadt, L.L.P.

(57) ABSTRACT

A base polymer for hot-melt adhesive, containing a propylenic polymer (A) having a tensile modulus of elasticity of 60 MPa or more, and an olefinic polymer (B) having a tensile modulus of elasticity of less than 60 MPa, wherein, relative to 100 parts by mass of the total amount of the propylenic polymer (A) and the olefinic polymer (B), the content of the propylenic polymer (A) is 1 part by mass or more and less than 50 parts by mass, and the content of the olefinic polymer (B) is more than 50 parts by mass and 99 parts by mass or less; and a hot-melt adhesive containing the base polymer, and further containing at least one of (C) a tackifier resin and (D) an oil.

12 Claims, 1 Drawing Sheet

| Discharge Rate | Evaluation | |
|---|---|---|
| | A | B |
| 3 cc/min | 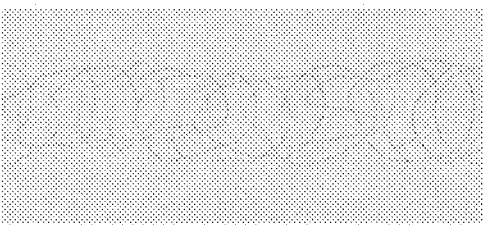 | 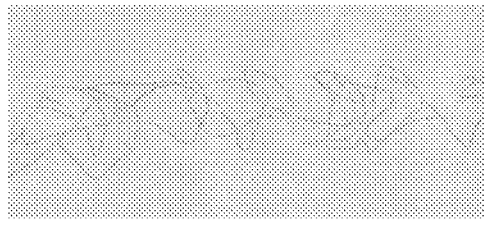 |
| 5 cc/min | 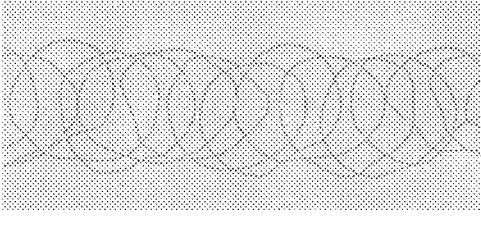 | 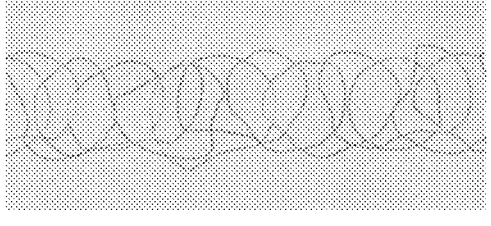 |

BASE POLYMER FOR HOT MELT ADHESIVE

TECHNICAL FIELD

The present invention relates to a base polymer for hot-melt adhesive containing two or more kinds of polymers, and a hot-melt adhesive containing it.

BACKGROUND ART

A hot-melt adhesive is a solvent-free adhesive and has a characteristic that instant bonding and high-speed bonding can be achieved since adhesiveness is exhibited after the adhesive is melted by heating and coated onto an adherend, followed by cooling to solidify the adhesive, and therefore has been used in a wide range of fields. Not only adherends to be bonded with such a hot-melt adhesive but also the conditions of use thereof are various. At present, various hot-melt adhesives for use in various applications have been developed and supplied to the market. Also for the conditions of use, various operating temperatures ranging from low temperatures to high temperatures are considered.

A propylenic polymer has heretofore been used as a base polymer for hot-melt adhesive. Above all, a low-molecular-weight polypropylene produced through polymerization using a metallocene-based catalyst has high flowability and is excellent in coatability when used as a hot-melt adhesive; and is excellent in adhesive strength with a low-polar substance such as polypropylene or the like and excellent in heat stability in melting under heat, it is favorably used as a base polymer for various kinds of hot-melt adhesives (PTL 1). In particular, it is suitable for spray coating for use in constructing hygienic materials such as paper diapers, sanitary goods, etc.

CITATION LIST

Patent Literature

PTL 1: WO 03/091289

SUMMARY OF INVENTION

Technical Problem

However, though the hot-melt adhesive using polypropylene as a base polymer described in PTL 1 could exhibit a high adhesive strength in bonding polypropylene-made nonwoven fabrics (hereinafter referred to as "PP nonwoven fabrics" as well) together, there has been a demand for further increasing the adhesive strength to other materials to constitute sanitary materials, especially to polyethylene-made films (hereinafter referred to as "PE film" as well). In addition, the hot-melt adhesive of PTL 1 has a problem in that the solidification speed thereof is slow. On the other hand, there is another problem in that when a general-purpose polymer is used, the coatability is poor.

The present invention relates to a base polymer for hot-melt adhesive excellent in coatability, having a high solidification speed, exhibiting a high adhesive strength in bonding PP nonwoven fabrics together, and further exhibiting a high adhesive strength in bonding PE film-PP nonwoven fabric, and to a hot-melt adhesive using the base polymer.

Solution to Problem

The present invention relates to the following [1] to [22].
[1] A base polymer for hot-melt adhesive, containing:
a propylenic polymer (A) having a tensile modulus of elasticity at 23° C. of 60 MPa or more, and
an olefinic polymer (B) having a tensile modulus of elasticity at 23° C. of less than 60 MPa, wherein:
relative to 100 parts by mass of the total amount of the propylenic polymer (A) and the olefinic polymer (B), the content of the propylenic polymer (A) is 1 part by mass or more and less than 50 parts by mass, and the content of the olefinic polymer (B) is more than 50 parts by mass and 99 parts by mass or less.
[2] The base polymer for hot-melt adhesive according to the above [1], wherein the content of the propylenic polymer (A) is 1 part by mass or more and 40 parts by mass or less, and the content of the olefinic polymer (B) is 60 parts by mass or more and 99 parts by mass or less.
[3] The base polymer for hot-melt adhesive according to the above [1] or [2], wherein the propylenic polymer (A) is a propylene homopolymer.
[4] The base polymer for hot-melt adhesive according to any one of the above [1] to [3], wherein the tensile modulus of elasticity at 23° C. of the propylenic polymer (A) is 90 MPa or more.
[5] The base polymer for hot-melt adhesive according to any one of the above [1] to [4], wherein the olefinic polymer (B) is an olefin copolymer or an olefin homopolymer.
[6] The base polymer for hot-melt adhesive according to any one of the above [1] to [5], wherein the olefinic polymer (B) is a copolymer of at least two selected from the group consisting of propylene, ethylene and α-olefins each having 4 to 24 carbon atoms, a propylene homopolymer, or an ethylene homopolymer.
[7] The base polymer for hot-melt adhesive according to any one of the above [1] to [6], wherein the olefinic polymer (B) is a copolymer of propylene, ethylene and 1-butene.
[8] The base polymer for hot-melt adhesive according to any one of the above [1] to [7], wherein the propylenic polymer (A) has a melting point of 120° C. or lower.
[9] The base polymer for hot-melt adhesive according to any one of the above [1] to [8], wherein the olefinic polymer (B) has a melting point of 50° C. or higher and 160° C. or lower.
[10] A hot-melt adhesive containing a base polymer for hot-melt adhesive according to any one of the above [1] to [9], and further containing at least one selected from the group consisting of (C) a tackifier resin and (D) an oil.
[11] A hot-melt adhesive containing a base polymer, which contains a propylenic polymer (A) having a tensile modulus of elasticity at 23° C. of 60 MPa or more, and an olefinic polymer (B) having a tensile modulus of elasticity at 23° C. of less than 60 MPa, and in which, relative to 100 parts by mass of the total amount of the propylenic polymer (A) and the olefinic polymer (B), the content of the propylenic polymer (A) is 1 part by mass or more and less than 50 parts by mass, and the content of the olefinic polymer (B) is more than 50 parts by mass and 99 parts by mass or less, the hot-melt adhesive satisfying the following (1) and (2):
  (1) the tensile modulus of elasticity at 23° C. of the base polymer is 400 Pa or less; and
  (2) the semi-crystallization time at 25° C. of the hot-melt adhesive is 5 minutes or less.
[12] The hot-melt adhesive according to the above [11], wherein the content of the propylenic polymer (A) is 1 part by mass or more and 40 parts by mass or less, and the content of the olefinic polymer (B) is 60 parts by mass or more and 99 parts by mass or less.
[13] The hot-melt adhesive according to the above [11] or [12], wherein the propylenic polymer (A) is a propylene homopolymer.

[14] The hot-melt adhesive according to any one of the above [11] to [13], wherein the tensile modulus of elasticity of the propylenic polymer (A) is 90 MPa or more.
[15] The hot-melt adhesive according to any one of the above [11] to [14], wherein the olefinic polymer (B) is an olefin copolymer or an olefin homopolymer.
[16] The hot-melt adhesive according to any one of the above [11] to [15], wherein the olefinic polymer (B) is a copolymer of at least two selected from the group consisting of propylene, ethylene and α-olefins each having 4 to 24 carbon atoms, a propylene homopolymer, or an ethylene homopolymer.
[17] The hot-melt adhesive according to any one of the above [11] to [16], wherein the olefinic polymer (B) is a copolymer of propylene, ethylene and 1-butene.
[18] The hot-melt adhesive according to any one of the above [11] to [17], wherein the propylenic polymer (A) has a melting point of 120° C. or lower.
[19] The hot-melt adhesive according to any one of the above [11] to [18], wherein the olefinic polymer (B) has a melting point of 50° C. or higher and 160° C. or lower.
[20] The hot-melt adhesive according to any one of the above [11] to [19], further containing at least one selected from the group consisting of (C) a tackifier resin and (D) an oil.
[21] A method of bonding a substrate to another substrate, including a step of melting a hot-melt adhesive according to any one of the above [10] to [20], and applying the melted hot-melt adhesive to at least one substrate, and a step of bonding another substrate to the applied hot-melt adhesive.
[22] A sanitary article containing a hot-melt adhesive according to any one of the above [10] to [20].

Advantageous Effects of Invention

According to the present invention, there can be provided a base polymer for hot-melt adhesive excellent in coatability, having a high solidification speed, exhibiting a high adhesive strength in bonding PP nonwoven fabrics together, and further exhibiting a high adhesive strength in bonding PE film-PP nonwoven fabric, and a hot-melt adhesive using the base polymer.

BRIEF DESCRIPTION OF DRAWING

FIG. 1 shows criteria for coatability evaluation in Examples.

DESCRIPTION OF EMBODIMENTS

The present invention is described in detail hereinunder. In this description, preferred definitions can be employed arbitrarily, and a combination of preferred embodiments is more preferred.
[Base Polymer]
The base polymer for hot-melt adhesive of the present invention contains a propylenic polymer (A) having a tensile modulus of elasticity at 23° C. of 60 MPa or more, and an olefinic polymer (B) having a tensile modulus of elasticity at 23° C. of less than 60 MPa. In the base polymer, relative to 100 parts by mass of the total amount of the propylenic polymer (A) and the olefinic polymer (B), the content of the propylenic polymer (A) is 1 part by mass or more and less than 50 parts by mass, and the content of the olefinic polymer (B) is more than 50 parts by mass and 99 parts by mass or less. The total content of the propylenic polymer (A) and the olefinic polymer (B) in the base polymer of the present invention is preferably 95% by mass or more, more preferably 98% by mass or more, even more preferably substantially 100% by mass.

For bonding PP nonwoven fabrics together or both PE film-PP nonwoven fabric in a well-balanced manner, it is effective to control the modulus of elasticity of the base polymer. The reasons are as mentioned below. For strongly bonding PP nonwoven fabrics together, it is preferable that the anchor effect of the adhesive is stronger, that is, the modulus of elasticity of the base polymer is higher. On the other hand, for bonding PE film-PP nonwoven fabric, the adhesive must be flexible so as to follow the PE film, and preferably has a lower modulus of elasticity. By controlling the blending amount of a polymer having a high modulus of elasticity and a polymer having a low modulus of elasticity, a base polymer for hot-melt adhesive that exhibits a well-balanced adhesiveness can be produced. For the above-mentioned reasons, by adding a small amount of the propylenic polymer (A) having a tensile modulus of elasticity at 23° C. of 60 MPa or more to the olefinic polymer (B) having a tensile modulus of elasticity at 23° C. of less than 60 MPa, the adhesiveness balance can be improved.

For improving coatability, it is effective to reduce the proportion of the high-molecular-weight component in the base polymer, that is, to add a polymer having a narrow molecular weight distribution. The reasons are as mentioned below. Coatability is related to the molecular weight distribution of hot-melt adhesive. When the molecular weight distribution of the base polymer is broad, the amount of the high-molecular-weight component is large. A high-molecular-weight component takes a long relaxation time, and therefore, in spreading a hot-melt adhesive by air for coating therewith, the line width of the hot-melt adhesive is confused owing to the stress applied to the high-molecular-weight component, therefore providing a cause to worsen the coatability. For preventing this, it is effective to use a polymer having a narrow molecular weight distribution. A polyolefin produced using a solid catalyst such as a Ziegler-Natta catalyst or the like has a broad molecular weight distribution, and therefore, by adding a polyolefin having a narrow molecular weight distribution thereto, the coatability is expected to improve.
[Propylenic Polymer (A)]
The tensile modulus of elasticity at 23° C. of the propylenic polymer (A) is, from the viewpoint of excellent coatability, high adhesive strength between PP nonwoven fabrics and high adhesive strength between PE film-PP nonwoven fabric, 60 MPa or more.

Preferably, the tensile modulus of elasticity at 23° C. of the propylenic polymer (A) is 65 MPa or more, more preferably 70 MPa or more, even more preferably 80 MPa or more, still more preferably 90 MPa or more, further more preferably 100 MPa or more, and is preferably 800 MPa or less, more preferably 700 MPa or less, still more preferably 600 MPa or less.

For the measurement method for the tensile modulus of elasticity, the method described in the section of Examples is referred to.

The propylenic polymer (A) is preferably at least one selected from a propylene homopolymer and a copolymer of propylene and any other olefin, and is more preferably a propylene homopolymer. The other olefin than propylene that may be contained in the propylenic polymer (A) includes ethylene and α-olefins each having 4 or more carbon atoms, and is more preferably ethylene. The content of the other olefin is, relative to the propylenic polymer (A), preferably 5% by mass or less, more preferably 3% by mass or less, even more preferably 1% by mass or less.

The α-olefin having 4 or more carbon atoms is preferably an α-olefin having 4 to 24 carbon atoms, more preferably an α-olefin having 4 to 12 carbon atoms, even more preferably an olefin having 4 to 8 carbon atoms. Specific examples of the α-olefin include 1-butene, 1-pentene, 4-methyl-1-pentene, 1-hexene, 1-octene, 1-decene, 1-dodecene, 1-tetradecene, 1-hexadecene, 1-octadecene, 1-eicocene, etc. In the present invention, one, two or more among these can be used.

More specific examples of the copolymer of propylene and any other olefin include at least one selected from the group consisting of a propylene-ethylene copolymer and a copolymer of propylene and an α-olefin having 4 or more carbon atoms.

(Melting Point)

The melting point of the propylenic polymer (A) is preferably 120° C. or lower. When the melting point is 120° C. or lower, the polymer is excellent in adhesive strength between nonwoven fabrics.

The melting point of the propylenic polymer (A) is, for realizing an excellent adhesive strength between nonwoven fabrics, preferably 118° C. or lower, more preferably 115° C. or lower. The melting point is, for easy handling, preferably 0° C. or higher, more preferably 40° C. or higher.

The method of measuring the melting point is described in the section of Examples.

(Weight-Average Molecular Weight (Mw))

Mw (weight-average molecular weight) of the propylenic polymer (A) is preferably 10,000 to 150,000. When Mw is 10,000 to 150,000, the polymer is excellent in adhesive strength between nonwoven fabrics.

Mw of the propylenic polymer (A) is, for realizing an excellent adhesive strength between nonwoven fabrics, preferably 20,000 to 130,000, more preferably 20,000 to 100,000.

(Mw/Mn)

Mw/Mn (weight-average molecular weight/number-average molecular weight) of the propylenic polymer (A) is preferably 2.5 or less. When Mw/Mn is 2.5 or less, the polymer is excellent in adhesive strength between nonwoven fabrics.

Mw/Mn of the propylenic polymer (A) is, for realizing an excellent adhesive strength between nonwoven fabrics, preferably 2.4 or less, more preferably 2.2 or less. Also preferably, Mw/Mn is 1.2 or more, more preferably 1.5 or more.

In the present invention, the weight-average molecular weight (Mw) and the number-average molecular weight (Mn) are measured using the apparatus under the condition described in the section of Examples.

The meso pentad fraction [mmmm] of the propylenic polymer (A) is, from the viewpoint of adhesive strength between nonwoven fabrics, preferably 10 to 80 mol %, more preferably 20 to 80 mol %, even more preferably 25 to 75 mol %, still more preferably 40 to 75 mol %, and further more preferably 50 to 75 mol %. The meso pentad fraction may be controlled by controlling the monomer concentration and the reaction pressure.

In the present invention, the meso pentad fraction is measured using the apparatus under the condition described in the section of Examples.

(Production Method for Propylenic Polymer (A))

The production method for the propylenic polymer (A) includes a method of producing a propylene homopolymer through homopolymerization of propylene using a metallocene-based catalyst, and a method of producing a propylene copolymer through copolymerization of propylene, and ethylene and/or an α-olefin having 4 or more carbon atoms.

Examples of the metallocene-based catalyst include catalysts obtained by combining a transition metal compound containing one or two ligands selected from a cyclopentadienyl group, a substituted cyclopentadienyl group, an indenyl group, a substituted indenyl group and the like as described in JP S58-19309 A, JP S61-130314 A, JP H03-163088 A, JP H04-300887 A, JP H04-211694 A, JP H01-502036 A and the like, or a transition metal compound, in which the above ligand is geometrically controlled, with a promoter.

Among metallocene catalysts, those with a transition metal compound where ligands form a crosslinked structure via a crosslinking group are preferred and, above all, a method of using a metallocene compound obtained by combining a transition metal compound where a crosslinked structure is formed via two crosslinking groups with a promoter is more preferred. Examples described in the paragraphs [0037] to [0084] in JP 2001-172325 A are referred to as preferred examples in the present invention.

The content of the propylenic polymer (A) is, from the viewpoint of excellent coatability, rapid solidification speed, high adhesive strength between PP nonwoven fabrics and high adhesive strength between PE film-PP nonwoven fabric, preferably 1 part by mass or more and less than 50 parts by mass relative to 100 parts by mass of the total amount of the propylenic polymer (A) and the olefinic polymer (B).

The content of the propylenic polymer (A) is, form the viewpoint of high adhesive strength between PP nonwoven fabrics, preferably 2 parts by mass or more, more preferably 3 parts by mass or more, even more preferably 4 parts by mass or more, relative to 100 parts by mass of the total amount of the propylenic polymer (A) and the olefinic polymer (B). In addition, the content is, from the viewpoint of coatability and from the viewpoint of high adhesive strength between PE film-PP nonwoven fabric, preferably 45 parts by mass or less, more preferably 40 parts by mass or less, even more preferably 35 parts by mass or less, still more preferably 30 parts by mass or less, further more preferably 25 parts by mass or less, relative to 100 parts by mass of the total amount of the propylenic polymer (A) and the olefinic polymer (B).

[Olefinic Polymer (B)]

The tensile modulus of elasticity at 23° C. of the olefinic polymer (B) is, from the viewpoint of excellent coatability, rapid solidification speed, high adhesive strength between PP nonwoven fabrics and high adhesive strength between PE film-PP nonwoven fabric, less than 60 MPa.

The tensile modulus of elasticity at 23° C. of the olefinic polymer (B) is preferably 50 MPa or less, more preferably 30 MPa or less. The tensile modulus of elasticity at 23° C. of the olefinic polymer (B) is preferably 0 MPa or more, more preferably 5 MPa or more, even more preferably 10 MPa or more, still more preferably 14 MPa or more.

The tensile modulus of elasticity is measured according to the method described in the section of Examples.

The olefinic polymer (B) is an olefin copolymer or an olefin homopolymer. The olefin copolymer is preferably a copolymer of at least two selected from the group consisting of ethylene and α-olefins, more preferably a copolymer of at least two selected from the group consisting of propylene, ethylene and α-olefins each having 4 to 24 carbon atoms, even more preferably a copolymer of propylene and any other olefin. The homopolymer is preferably a propylene homopolymer or an ethylene homopolymer.

The other olefin than propylene contained in the olefinic polymer (B) includes at least one selected from the group consisting of ethylene and α-olefins each having 4 or more carbon atoms, more preferably at least one selected from the group consisting of ethylene and α-olefins each having 4 to 24 carbon atoms.

The α-olefin having 4 or more carbon atoms is preferably an α-olefin having 4 to 24 carbon atoms, more preferably an α-olefin having 4 to 20 carbon atoms, even more preferably an α-olefin having 4 to 12 carbon atoms, still more preferably an α-olefin having 4 to 8 carbon atoms. Specific examples of the α-olefin include 1-butene, 1-pentene, 4-methyl-1-pentene, 1-hexene, 1-octene, 1-decene, 1-dodecene, 1-tetradecene, 1-hexadecene, 1-octadecene, 1-eicocene, etc. Among these, 1-butene and 1-octene are preferred. In the present invention, one, two or more among these can be used.

More specifically, the olefinic polymer (B) is preferably a copolymer of propylene, and at least one selected from the group consisting of ethylene and α-olefins each having 4 to 24 carbon atoms. The olefinic polymer (B) is preferably a copolymer of propylene, ethylene and α-olefin having 4 to 24 carbon atoms, more preferably at least one selected from a copolymer of propylene, ethylene and 1-butene, and an ethylene-1-octene copolymer, and even more preferably a copolymer of propylene, ethylene and 1-butene.

In the olefinic copolymer (B), preferably, the amount of the structural unit derived from propylene is preferably 30 to 90 mol %, more preferably 40 to 80 mol %, even more preferably 50 to 80 mol %

In the olefinic polymer (B), the amount of the structural unit derived from ethylene is, for increasing the adhesive strength between PE film and nonwoven fabric, preferably 1 to 30 mol %, more preferably 6 to 25 mol %, even more preferably 8 to 20 mol %.

In the olefinic polymer (B), the amount of the structural unit derived from an α-olefin having 4 to 24 carbon atoms is, for increasing the adhesive strength between PE film and nonwoven fabric, preferably 1 to 30 mol %, more preferably 5 to 23 mol %, even more preferably 10 to 20 mol %.

The olefinic polymer (B) is more preferably an amorphous olefinic polymer. The amorphous olefinic polymer is a homopolymer or a copolymer of one or more selected from the group consisting of linear or branched α-olefins or dienes each having 2 to 24 carbon atoms, and includes, though not specifically limited thereto, a polybutene, a polybutadiene, a polyisoprene, an ethylene-propylene copolymer, an ethylene-propylene-1-butene copolymer, a liquid poly-α-olefin, an isoparaffin. In addition, a paraffinic process oil or an isoparaffinic process oil to be mentioned below can also be used.

The tensile modulus of elasticity of the amorphous olefinic polymer that is liquid at room temperature (23° C.) is 0 Pa.

The polybutene includes a homo or copolymer of isobutene or normal butene, and hydrogenated products thereof. Commercial products of polybutene include "Nisseki Polybutene LV-7", "Nisseki Polybutene LV-50", "Nisseki Polybutene LV-100", "Nisseki Polybutene HV-15", "Nisseki Polybutene HV-35", "Nisseki Polybutene HV-50", "Nisseki Polybutene HV-100", "Nisseki-Polybutene HV-190", "Nisseki Polybutene HV-300", "Nisseki Polybutene SV-7000" (trade names, manufactured by JX Nippon Oil & Energy Corporation), "Nissan Polybutene ON", "Nissan Polybutene 06N", "Nissan Polybutene 015N", "Nissan Polybutene 3N", "Nissan Polybutene 5N", "Nissan Polybutene 10N", "Nissan Polybutene 30N", "Nissan Polybutene 200N" (trade names, manufactured by NOF Corporation), "Tetrax 3T", "Tetrax 4T", "Tetrax 5T", "Tetrax 6T", "Himol 4H", "Himol 5H", "Himol 5.5H", "Himol 6H" (trade names, manufactured by JX Nippon Oil & Energy Corporation), "Glissopal" (trade name, manufactured by BASF AG), "Indopol H-300", "Indopol H-1900" (trade names, manufactured by INEOS Chemicals Corporation), "Parapol 950", "Parapol 1300" (trade names, manufactured by Exxon Mobile Chemical Corporation), etc.

The polybutadiene includes a homo or copolymer of 1,2-butaiene or 1,4-butadiene, and hydrogenated products thereof, which may have a hydroxyl group at the terminal. Commercial products of polybutadiene include "Nisso PB B-1000", "Nisso PB B-2000", "Nisso PB B-3000", "Nisso PB BI-2000", "Nisso PB BI-3000" (trade names, manufactured by Nippon Soda Co., Ltd.), "PolyVEST 110", "PolyVEST 130" (trade names, manufactured by Evonik Industries AG), "Ricon 130", "Ricon 131", "Ricon 134", "Ricon 144", "Ricon 150", "Ricon 152", "Ricon 153", "Ricon 154", "Ricon 156", "Ricon 157" (trade names, manufactured by Cray Valley SA), "UBEPOL BR" series (trade name, manufactured by Ube Industries, Ltd.), "JSR RB" series (trade name, manufactured by JSR Corporation), "Nipol BR" series (trade name, manufactured by Nippon Zeon Corporation), "Poly bd™ R-45HT", "Poly bd™ R-15HT" (trade names, manufactured by Idemitsu Kosan Co., Ltd.), etc.

The polyisoprene includes an isoprene homopolymer, an isoprene copolymer, and hydrogenated products thereof, which may have a hydroxyl group at the terminal. Commercial products of polyisoprene include "Nipol IR" series (trade name, manufactured by Nippon Zeon Corporation), "Kuraprene" series (trade name, manufactured by Kuraray Co., Ltd.), "JSR IR" series (trade name, manufactured by JSR Corporation), Polyip™, "EPOL™" (trade names, manufactured by Idemitsu Kosan Co., Ltd.), etc.

Commercial products of ethylene-propylene copolymer include "JSR EP" series (trade name, manufactured by JSR Incorporation), "Tafmer" series (trade name, manufactured by Mitsui Chemicals, Inc.), etc.

The ethylene-propylene-1-butene copolymer includes "Vestoplast" series (trade name, manufactured by Evonik AG), etc.

Commercial products of liquid poly-α-olefin include "Lucant" series (trade name, manufactured by Mitsui Chemicals, Inc.), "SpectraSyn Elite" series, "SpectraSyn Plus" series, "SpectraSyn" series (trade names, manufactured by Exxon Mobile Chemical Corporation", "Durasyn" series, "Silkflo" series (trade name, manufactured by INEOS Corporation), "HS Dimer" series (trade name, manufactured by Hokoku Corporation), etc.

The isoparaffin is an oligomer produced by polymerizing one or two or more components of isobutene, normal butene, normal propylene and isopropylene, and hydrogenated products thereof. The polymerization degree of the oligomer is preferably 3 to 10.

Commercial products of isoparaffin include "IP Solvent 1016", "IP Solvent 1620", "IP Solvent 2028", "IP Solvent 2835", "IP Clean LX" (trade names, manufactured by Idemitsu Kosan Co., Ltd.), etc.

The melt viscosity at 190° C. of the olefinic polymer (B) is preferably 2,000 mPa·s or more, more preferably 3,000 mPa·s or more, even more preferably 5,000 mPa·s or more. The melt viscosity is preferably 15,000 mPa·s or less, more preferably 13,000 mPa·s or less, even more preferably 10,000 mPa·s or less.

(Melting Point)

The melting point of the olefinic polymer (B) is preferably 50° C. or higher and 160° C. or lower. When the melting point is 50° C. or higher and 160° C. or lower, the adhesive strength between PE film and nonwoven fabric is excellent.

The melting point of the olefinic polymer (B) is, for realizing an excellent adhesive strength between PE film and nonwoven fabric, preferably 70° C. or higher, more preferably 80° C. or higher. The melting point is, also for realizing an excellent adhesive strength between PE film and nonwoven fabric, preferably 160° C. or lower, more preferably 130° C. or lower, even more preferably 100° C. or lower.

(Weight-Average Molecular Weight (Mw))

Mw (weight-average molecular weight) of the olefinic polymer (B) is preferably 10,000 to 150,000. When Mw is 10,000 to 150,000, the adhesive strength between nonwoven fabric and nonwoven fabric is excellent.

Mw of the olefinic polymer (B) is, for realizing an excellent adhesive strength between nonwoven fabric and nonwoven fabric, more preferably 20,000 to 130,000, even more preferably 20,000 to 100,000.

(Mw/Mn)

Mw/Mn (weight-average molecular weight/number-average molecular weight) of the olefinic polymer (B) is preferably 1.5 or more and 7.0 or less. When Mw/Mn is 1.5 or more and 6.0 or less, the flowability and coatability in melt is excellent.

Mw/Mn of the olefinic polymer (B) is, for realizing excellent coatability, more preferably 1.5 or more and 6.5 or less.

(Production Method for Olefinic Polymer (B))

The production method for the olefinic polymer (B) includes, though not specifically limited thereto, a method for producing a copolymer through polymerization of at least two selected from the group consisting of ethylene and α-olefins using a Ziegler-Natta catalyst or a metallocene catalyst.

Examples of commercial products of the olefinic polymer (B) include "Vestoplast 708" (manufactured by Evonik Industries AG), "Affinity GA1950" (manufactured by The Dow Chemical Company), etc.

The content of the olefinic polymer (B) is, from the viewpoint that the polymer is excellent in coatability, has a rapid solidification, exhibits a high adhesive strength between PP nonwoven fabrics and further exhibits a high adhesive strength between PE film and PP nonwoven fabric, more than 50 parts by mass and 99 parts by mass or less relative to 100 parts by mass of the total amount of the propylenic polymer (A) and the olefinic polymer (B).

The content of the olefinic polymer (B) is, from the viewpoint of coatability and high adhesive strength between PE film and PP nonwoven fabric, preferably 55 parts by mass or more, more preferably 60 parts by mass or more, even more preferably 65 parts by mass or more, still more preferably 70 parts by mass or more, further more preferably 75 parts by mass or more, relative to 100 parts by mass of the total amount of the propylenic polymer (A) and the olefinic polymer (B). Also from the viewpoint of increasing the solidification speed and from the viewpoint of realizing high adhesive strength between PP nonwoven fabrics, the content is preferably 98 parts by mass or less, more preferably 97 parts by mass or less, even more preferably 96 parts by mass or less, relative to 100 parts by mass of the total amount of the propylenic polymer (A) and the olefinic polymer (B).

[Hot-Melt Adhesive]

The hot-melt adhesive of the present invention contains a propylenic polymer (A) and an olefinic polymer (B), and may further contain at least one selected from the group consisting of (C) a tackifier resin, (D) an oil and (E) a wax, and preferably contains at least one selected from the group consisting of (C) a tackifier resin and (D) an oil, more preferably (C) a tackifier resin and (D) an oil.

The hot-melt adhesive of the present invention may contain, as needed, various additives such as a plasticizer, an inorganic filler, an antioxidant, etc.

In particular, the base polymer of the present invention is excellent in applicability to hot-melt adhesive, and can be used for controlling solidification speed and melt viscosity. Further, the base polymer is effective for improving handling performance through prevention of oil bleeding and inhibition of sticky feel. For example, it is considered that by adding a base polymer having a low tensile modulus of elasticity, the open time can be prolonged, and by adding a base polymer having a high tensile modulus of elasticity, the set time can be shortened.

((C) Tackifier Resin)

Examples of the tackifier resin include those that are solid, semisolid or liquid at room temperature, such as hydrogenated derivatives of aliphatic hydrocarbon petroleum resins, rosin derivative resins, polyterpene resins, petroleum resins, oil-soluble phenolic resins, etc. One of them may be used singly or two or more thereof may be used in combination. In the present invention, hydrogenated products are preferably used in consideration of the miscibility thereof with base polymer. Above all, hydrogenated products of petroleum resins excellent in heat stability are more preferred.

Commercial products of tackifier resin include "I-Mary P-125", "I-Mary P-100", "I-Mary P-90" (all by Idemitsu Kosan Co., Ltd.), "Umex 1001" (manufactured by Sanyo Chemical Industries, Ltd.), "Hilets T1115" (manufactured by Mitsui Chemicals, Inc.), "Clearon K100" (manufactured by Yasuhara Chemical Co., Ltd.), "ECR-227", "Escorez 2101", "Escorez 5000" series (all by Tonen Chemical Corporation), "Alcon P100" (manufactured by Arakawa Chemical Industries, Ltd.), "Regalrez 1078" (manufactured by Hercules Inc.) (all trade names), etc.

The content of the tackifier resin in the hot-melt adhesive of the present invention is, from the viewpoint of increasing adhesiveness, coatability and improving wettability to adherends through viscosity reduction, preferably 20 to 200 parts by mass, relative to 100 parts by mass of the base polymer, more preferably 30 to 150 parts by mass, even more preferably 50 to 120 parts by mass.

The softening point of the tackifier resin is not specifically limited. However, when the softening point is too high, the coatability of the hot-melt adhesive worsens owing to viscosity increase, and when the softening point is too low, the heat stability of the hot-melt adhesive worsens and, if so, scorching may occur in a melter to have some negative influence on the adhesiveness and to cause offensive odor emission. For these reasons, the softening point of the tackifier resin is preferably 80 to 130° C., more preferably 85 to 120° C., even more preferably 90 to 110° C.

((D) Oil)

Examples of the oil include paraffinic process oil, naphthenic process oil, isoparaffinic oil, etc.

Commercial products of paraffinic process oil include "Diana Process Oil PW-32", "Diana Process Oil PW-90", "Diana Process Oil PW-150", "Diana Process Oil PS-32", "Diana Process Oil PS-90", "Diana Process Oil PS-430", "IP Solvent 2028", "IP Solvent 2835" (trade names, manufactured by Idemitsu Kosan Co., Ltd.), "Kaydol Oil", "ParaLux Oil" (trade names, manufactured by Chevron USA Corporation), "Ragalrez101" (trade name, manufactured by Eastman Chemicals Corporation).

Commercial products of isoparaffinic oil include "NA Solvent Series" (trade name, manufactured by NOF Corporation), etc.

The oil content in the hot-melt adhesive of the present invention is, from the viewpoint of increasing adhesiveness, coatability and improving wettability to adherends through viscosity reduction, preferably 5 to 200 parts by mass relative to 100 parts by mass of the base polymer, more preferably 10 to 100 parts by mass, even more preferably 20 to 50 parts by mass.

((E) Wax)

The hot-melt adhesive of the present invention may contain a wax, as needed.

Examples of the wax include animal wax, vegetable wax, carnauba wax, candelilla wax, Japan wax, bees wax, mineral wax, petroleum wax, paraffin wax, microcrystalline wax, petrolatum, higher fatty acid wax, higher fatty acid ester wax, Fischer-Tropsch wax, etc.

However, the wax content in the hot-melt adhesive of the present invention is, from the viewpoint of improving coatability, preferably less than 25 parts by mass relative to 100 parts by mass of the base polymer, and more preferably no wax is added to the adhesive. Increase in wax addition worsens coatability.

(Other Additives)

Examples of the plasticizer include phthalates, adipates, fatty acid esters, glycols, epoxy-type polymer plasticizers, etc.

Examples of the inorganic filler include talc, calcium carbonate, barium carbonate, wollastonite, silica, clay, mica, kaolin, titanium oxide, diatomaceous earth, urea resin, styrene beads, starch, barium sulfate, calcium sulfate, magnesium silicate, magnesium carbonate, alumina, quartz powder, etc.

Examples of the antioxidant include phosphorus-containing antioxidants such as trisnonylphenyl phosphite, distearyl pentaerythritol diphosphite, "Adekastab 1178" (manufactured by ADEKA Corporation), "Sumilizer TNP" (manufactured by Sumitomo Chemical Co., Ltd.), "Trgafos 168" (manufactured by BASF Corporation), "Sandstab P-EPQ" (manufactured by Sandoz Japan Ltd.), etc.; phenolic antioxidants such as 2,6-di-t-butyl-4-methylphenol, n-octadecyl-3-(3',5'-di-t-butyl-4'-hydroxyphenyl) propionate, "Sumilizer BHT" (manufactured by Sumitomo Chemical Co., Ltd.), "Irganox 1010" (manufactured by BASF Corporation), etc.; sulfur-containing antioxidants such as dilauroyl-3,3'-thiodipropionate, pentaerythritol tetrakis(3-laurylthiopropionate), "Sumilizer TPL" (manufactured by Sumitomo Chemical Co., Ltd.), "DLTP "Yoshitomi"" (manufactured by Mitsubishi Chemical Corporation), "AntiOx L" (manufactured by NOF Corporation), etc.

[Production Method for Hot-Melt Adhesive]

The hot-melt adhesive of the present invention can be produced by dry-blending a propylenic polymer (A) and an olefinic polymer (B) as a base polymer and preferably at least one selected from (C) a tackifier resin and (D) an oil, and further optionally any other additives, using a Henschel mixer or the like, followed by melt-kneading the blend in a single-screw or twin-screw extruder, or a Plastomill, a Banbury mixer or the like.

As described above, the hot-melt adhesive of the present invention preferably satisfies the following (1) and (2), and more preferably further satisfies (3).

(1) The tensile modulus of elasticity at 23° C. of the base polymer is 400 MPa or less.

(2) The semi-crystallization time at 25° C. of the hot-melt adhesive is 5 minutes or less.

(3) The elongation at break at 23° C. of the base polymer is 150% or more and 1,200% or less.

(1) Tensile Modulus of Elasticity

From the viewpoint of the followability of the hot-melt adhesive to adherends, from the viewpoint of the adhesiveness thereof to rough surfaces of adherends and from the viewpoint of the anchor effect for rough surfaces of adherends, the hot-melt adhesive preferably has suitable flexibility. From these viewpoints, the tensile modulus of elasticity at 23° C. of the base polymer is preferably 400 MPa or less, more preferably 350 MPa or less, even more preferably 300 MPa or less, still more preferably 250 MPa or less, further more preferably 200 MPa or less, still further more preferably 150 MPa or less.

From the viewpoint of adhesiveness, the tensile modulus of elasticity is preferably lower, and the lower limit thereof is not specifically limited, that is, the measurement limit value is the lower limit. Specifically, the tensile modulus of elasticity is preferably 1 MPa or more, more preferably 5 MPa or more, even more preferably 10 MPa or more.

The tensile modulus of elasticity of the base polymer of the present invention is measured according to the method described in the section of Examples.

The tensile modulus of elasticity of the base polymer of the present invention can be controlled to fall within a desired range by varying the polymerization condition (reaction temperature, reaction time, catalyst, promoter) for the propylenic polymer (A) and by varying the component, the polymerization condition and the blending amount of the olefinic polymer (B).

(2) Semi-crystallization Time

The semi-crystallization time in the present invention refers to a time from the start of isothermal crystallization until the integral value of the calorific value becomes 50% when the integral value of the calorific value from the start of isothermal crystallization until the completion of crystallization is taken as 100%.

If the semi-crystallization time is too long, the solidification time of the hot-melt adhesive is too long (the solidification rate is low), and therefore, it is not suitable as the hot-melt adhesive. From such a viewpoint, the semi-crystallization time at 25° C. of the hot-melt adhesive is preferably 5 minutes or less, more preferably 4 minutes or less, even more preferably 3 minutes or less. From the viewpoint of the solidification rate of the hot-melt adhesive, the semi-crystallization time is preferably shorter, and the lower limit thereof is not particularly limited, and a measurement limit value becomes the lower limit, but the measurement limit varies depending on the measurement device. The measurement limit value in a device to be used for the method described in Examples of this description is 1 minute.

The semi-crystallization time of the hot-melt adhesive of the present invention is measured according to the method described in the section of Examples.

The semi-crystallization time of the hot-melt adhesive of the present invention can be controlled to fall within a desired range by varying the polymerization condition (reaction temperature, reaction time, catalyst, promoter) for the propylenic polymer (A), and by varying the component, the polymerization condition and the blending amount of the olefinic polymer (B). For shortening the semi-crystallization time of the hot-melt adhesive, it is effective to add a base polymer component having a short semi-crystallization time. This is because, by adding a polymer having a short semi-crystallization time, the crystallization-initiating part of the polymer acts as a starting point to facilitate crystallization.

(3) Elongation at Break

From the viewpoint of the adhesive strength between a hot-melt adhesive and an adherend, in order to bring the hot-melt adhesive into close contact with the concave-convex surface of the adherend, it is preferred that the hot-melt adhesive is moderately soft. On the other hand, if the hot-melt adhesive is too soft, it is easily peeled off. From such a viewpoint, the elongation at break at 23° C. of the base polymer to be used is preferably 150% or more, more preferably 300% or more, even more preferably 500% or more, still more preferably 700% or more, further more preferably 800% or more, and is also preferably 1,200% or less, more preferably 1,000% or less, even more preferably 900% or less.

The elongation at break of the base polymer of the hot-melt adhesive of the present invention is measured according to the method described in the section of Examples.

The elongation at break of the hot-melt adhesive can be controlled to fall within a desired range by varying the polymerization condition (reaction temperature, reaction time, catalyst, promoter) for the propylenic polymer (A), and by varying the component, the polymerization condition and the blending amount of the olefinic polymer (B).

When the melt viscosity at 160° C. of the hot-melt adhesive is too high, the adhesive is difficult to apply, and must be melted at a higher temperature, for which, therefore, the energy cost increases. Accordingly, the melt viscosity at 160° C. of the hot-melt adhesive is preferably 12,000 mPa·s or less, more preferably 1,000 to 10,000 mPa·s, even more preferably 1,500 to 8,000 mPa·s, still more preferably 2,000 to 6,000 mPa·s. The melt viscosity is measured according to the method described in the section of Examples.

The hot-melt adhesive of the present invention is excellent in adhesiveness to various substrates containing a low-polar substance such as a polyolefin or the like, and is excellent in heat stability in melting under heat, and is therefore favorably used, for example, for sanitary materials, for packaging, for bookmaking, for fibers, for woodworking, for electric materials, for can manufacturing, for construction, for filters, for low-pressure molding, for bag manufacturing, etc.

In particular, the hot-melt adhesive is favorably used for bonding of polyolefinic materials, and since a base polymer containing both a component having a high modulus of elasticity and a component having a low modulus of elasticity is used, the hot-melt adhesive exhibits well-balanced adhesive performance, and can be used, for example, for bonding polyolefin nonwoven fabric-polyolefin nonwoven fabric, or bonding polyolefin film-polyolefin nonwoven fabric. Preferably, it is used for bonding PP nonwoven fabric-PP nonwoven fabric, or for bonding PE film-PP nonwoven fabric. Consequently, hygienic goods such as paper diapers, sanitary goods and the like containing the hot-melt adhesive of the present invention are preferred.

In addition, since a polyolefin having a narrow molecular weight distribution is used as the base polymer, the content of a high-molecular-weight component therein reduces, and the hot-melt adhesive can be favorably used in spray coating as the coating method using it.

The tensile modulus of elasticity at 23° C. of the hot-melt adhesive of the present invention is, from the viewpoint of adhesiveness balance, preferably 0.8 to 10 MPa, more preferably 0.9 to 8 MPa, even more preferably 1 to 5 MPa.

The tensile modulus of elasticity of the hot-melt adhesive of the present invention is measured according to the method described in the section of Examples.

[Bonding Method]

The bonding method of the present invention is a method of bonding a substrate to another substrate, and includes a step of melting the hot-melt adhesive of the present invention, and applying it to at least one substrate, and a step of bonding another substrate to the applied hot-melt adhesive.

EXAMPLES

Next, the present invention will be described in more detail with reference to Examples, but the present invention is by no means limited to these Examples. In Examples of this description, the physical properties were measured according to the methods described below.

<Tensile Modulus of Elasticity and Elongation at Break of Base Polymer>

A sample of the base polymer was press-molded to prepare a test piece, and the tensile modulus of elasticity and the elongation at break of the base polymer were measured according to JIS K 7113 under the following condition.

Test piece (No. 2 dumbbell), thickness: 1 mm
Cross head rate: 100 mm/min
Load cell: 100 N
Measurement temperature: 23° C.

<Melting Point>

Using a differential scanning calorimeter "DSC-7" (manufactured by PerkinElmer Co., Ltd.), 10 mg of a sample of the base polymer was kept in a nitrogen atmosphere at −10° C. for 5 minutes, and then heated at 10°/min to draw a melting endothermic curve. The peak top of the peaks observed on the highest temperature side of the curve was referred to as the melting point (Tm-D).

<Weight-Average Molecular Weight (Mw), Number-Average Molecular Weight (Mn), and Molecular Weight Distribution (Mw/Mn)>

The weight-average molecular weight (Mw) and the number-average molecular weight (Mn) were polystyrene-equivalent ones measured using the following apparatus under the following condition, and the molecular weight distribution (Mw/Mn) was calculated from the weight-average molecular weight (Mw) and the number-average molecular weight (Mn)

<GPC Measuring Apparatus>

Column: "TOSO GMHHR-H(S)HT" (manufactured by Tosoh Corporation)
Detector: RI detector for liquid chromatography, "Waters 150C" (manufactured by Waters Corporation)

<Measurement Condition>

Solvent: 1,2,4-trichlorobenzene
Measurement temperature: 145° C.
Flow rate: 1.0 mL/min
Sample concentration: 2.2 mg/mL
Injection amount: 160 μL
Calibration curve: Universal Calibration
Analysis software: HT-GPC (ver. 1.0)

<Meso Pentad Fraction [mmmm]>

The meso pentad fraction [mmmm] was determined in accordance with the method proposed in "Macromolecules, 6, 925 (1973)" by A. Zambelli et al., and is a meso fraction and a racemic meso racemic meso fraction in a pentad unit in a polypropylene molecular chain measured with the signal of a methyl group in the $^{13}$C-NMR spectrum.

$^{13}$C-NMR spectrometry was carried out using the following apparatus under the following condition.

Apparatus: $^{13}$C-NMR spectrometer, "JNM-EX400" (manufactured by JEOL, Ltd.)
Method: proton complete decoupling method
Concentration: 220 mg/mL
Solvent: mixed solvent of 1,2,4-trichlorobenzene and deuterated benzene at 90:10 (volume ratio)
Temperature: 130° C.
Pulse width: 45°
Pulse repetition time: 4 seconds
Accumulation: 10,000 times
<Calculation Formulae>
M=m/S×100
R=γ/S×100
S=Pββ+Pαβ+Pαγ
S: signal intensity of carbon atoms of side-chain methyl in all propylene units
Pββ: 19.8 to 22.5 ppm
Pαβ: 18.0 to 17.5 ppm
Pαγ: 17.5 to 17.1 ppm
γ: racemic pentad chain: 20.7 to 20.3 ppm
m: meso pentad chain: 21.7 to 22.5 ppm
[Propylenic Polymer (A)]
Propylenic Polymer (A1)

Synthesis Example 1

Production of Complex (1) "((1,2'-dimethylsilylene)(2,1'-dimethylsilylene)-bis(3-trimethylsilylmethylindenyl)zirconium dichloride)"

According to the description of Reference Example 1 in Japanese Patent 4053993, (1,2'-dimethylsilylene)(2,1'-dimethylsilylene)-bis(3-trimethylsilylmethylindenyl)zirconium dichloride was synthesized.

Production Example 1

Production of Propylenic Polymer (A1)

26 L/h of n-heptane, 7.7 mmol/h (0.3 mmol/L) of triisobutyl aluminum, and further a catalyst component prepared by previous contact of dimethylanilinium tetrakispentafluorophenyl borate, the complex (1), and propylene in an amount of 3.0 mol/h as zirconium were continuously supplied in a stainless reactor having an inner volume of 0.25 m$^3$ and equipped with a stirrer.

Propylene and hydrogen were continuously supplied thereinto in such a manner that, at a polymerization temperature of 80° C., the hydrogen concentration in the vapor phase part could be 22 mol % and the total pressure in the reactor could be kept at 1.0 MPa·G An antioxidant was added to the resultant polymerization solution to be in an amount of 1,000 ppm, and the solvent was removed to give a propylenic polymer (A1).

Propylenic Polymer (A2)

Synthesis Example 2

Production of Complex (2) "(1,2'-dimethylsilylene)(2,1'-dimethylsilylene)(indenyl)(3-trimethylsilylmethylindenyl)zirconium dichloride"

According to the description of Example 5 in Japanese Patent 4053993, (1,2'-dimethylsilylene)(2,1'-dimethylsilylene)(indenyl)(3-trimethylsilylmethylindenyl)zirconium dichloride was synthesized.

Production Example 2

Production of Propylenic Polymer (A2)

25 L/h of n-heptane, 9.7 mmol/h (6.9 mmol/L) of triisobutyl aluminum, and further a catalyst component prepared by previous contact of dimethylanilinium tetrakispentafluorophenyl borate, the complex (2), triisobutyl aluminum and propylene in an amount of 24 μmol/h as zirconium were continuously supplied in a stainless reactor having an inner volume of 0.16 m$^3$ and equipped with a stirrer. Propylene was continuously supplied thereinto in such a manner that, at a polymerization temperature of 70° C., the total pressure in the reactor could be kept at 0.48 MPa·G. An antioxidant was added to the resultant polymerization solution to be in an amount of 1,000 ppm, and the solvent was removed to give a propylenic polymer (A2).

Propylenic Polymer (A3)

Synthesis Example 3

Production of Complex (3) "(1,2'-dimethylsilylene)(2,1'-dimethylsilylene)-bis(indenyl)zirconium dichloride"

According to the description of Example 1 in JP 2000-256411 A, (1,2'-dimethylsilylene)(2,1'-dimethylsilylene)-bis(indenyl)zirconium dichloride was synthesized.

Production Example 3

Production of Propylenic Polymer (A3)

Heptane (4 L), triisobutyl aluminum (2 M, 2 mL, 4 mmol), a heptane slurry of the complex (3) (10 mol/mL, 0.3 mL, 3 μmop, and a heptane slurry of dimethylanilinium tetrakis(pentafluorophenyl)borate (10 μmol/mL, 0.9 mL, 9.0 μmol) were added to a hot and dry 10-liter autoclave, and further hydrogen (0.01 MPa) was introduced thereinto. With stirring, propylene was introduced in such a manner that the total pressure could reach 0.66 MPa, and at the same time, this was heated up to 60° C. After polymerized for 2 hours, the polymerization was stopped by 5 mL of ethanol, and after depressurized, the reaction product was dried under reduced pressure to give a propylenic polymer (A3).

[Olefinic Polymer (B)]
Olefinic Polymer (B1)

Ethylene-propylene-1-butene copolymer "Vestoplast 708" (manufactured by Evonik AG, weight-average molecular weight: 75,000, ethylene/propylene/butane=11.3/64.8/23.9 (ratio by mass), tensile modulus of elasticity: 15.3 MPa, melt viscosity: 8,000 mPa·s) Olefinic Polymer (B2)

Ethylene-1-octent copolymer "Affinity GA 1950" (manufactured by The Dow Chemical Company, tensile modulus of elasticity: 15.2 MPa)

[Tackifier Resin]

"I-MARV P-100" (manufactured by Idemitsu Kosan Co., Ltd.)

[Oil]

"Diana Process Oil PW-90" (manufactured by Idemitsu Kosan Co., Ltd.)

The physical properties of the polymers used in Examples were measured and shown in Table 1 below.

TABLE 1

|  | [mmmm] (mol %) | Tensile Modulus of Elasticity (MPa) | Melting Point (° C.) | Mw | Mw/Mn |
|---|---|---|---|---|---|
| Propylenic Polymer (A1) | 46 | 94 | 75.3 | 49,500 | 2.1 |
| Propylenic Polymer (A2) | 57 | 261.9 | 94.5 | 48,300 | 1.9 |
| Propylenic Polymer (A3) | 70 | 541.3 | 114.1 | 52,000 | 2.0 |
| Olefinic Polymer (B1) | — | 15.3 | 82.3 | 48,900 | 6.1 |
| Olefinic Polymer (B2) | — | 15.2 | 67.6 | 37,800 | 1.8 |

[Production of Resin Composition for Hot-Melt Adhesive]

The propylenic polymer (A), the olefinic polymer (B), the tackifier resin and the oil were blended in the ratio (part by mass) shown in the tables, put in a 1-liter stainless container and melted by heating with a drier at 180° C. for 30 minutes, and then the melt was set in a mantle heater, heated at 210° C. and well stirred with a rotary stirrer to produce a hot-melt adhesive.

[Adhesive Strength]

A spiral spray gun was set in an HMA coater system (manufactured by MEC Co., Ltd.), and a substrate coated with the hot-melt adhesive and a substrate to be bonded thereto were bonded to produce a laminate.

As the substrate to be coated, a PP nonwoven fabric (SMS 3 layers, 17 g/m$^2$, 150 mm width) or a vapor-pervious PE film (20 g/m$^2$, 150 mm width) was used, and as the substrate to be bonded, the PP nonwoven fabric (as above) was used, and these were bonded at a line speed of 150 m/min.

Regarding the coating condition with the spiral spray gun (nozzle diameter, about 0.5 mm), the melting temperature of the hot-melt adhesive was 150° C., the spray gun temperature was 150° C. and the hot air temperature was 180° C. The coating amount with the hot-melt adhesive was 3, 4 or 5 g/m$^2$, and the hot air pressure was so controlled that the coated spiral width could be about 15 mm. After coating, the pressure for bonding with a press roller was 0.1 MPa, and the open time was about 0.1 seconds.

The laminate bonded with the hot-melt adhesive was cut in a 25 mm width in the vertical direction to the substrate traveling direction (cross direction, CD) to give a test piece for measurement of the T-direction peeling adhesive strength. The test piece was cured at 23° C. and 50% RH for 24 hours or more, and then subjected to the T-direction peeling test in the same environment.

In the tables, the adhesive strength test results of the PE film-PP nonwoven fabric are shown as "PE/NW", and the adhesive strength test results of the PP nonwoven fabric-PP nonwoven fabric are as "NW/NW".

[Semi-Crystallization Time]

Using a differential scanning calorimeter "DSC-8500" (manufactured by PerkinElmer Co., Ltd.), the semi-crystallization time was measured according to the following method.

The hot-melt adhesive shown in the tables was melted by heating at 220° C. for 5 minutes, then cooled down to 25° C. at 320° C./min, and the time-dependent change in the calorific value in the isothermal crystallization process at 25° C. was measured, and the semi-crystallization time was determined.

[Tensile Modulus of Elasticity]

A sample of the hot-melt adhesive was press-molded to prepare a test piece, and the tensile modulus of elasticity thereof was measured according to JIS K 7113 under the following condition.

Test piece (No. 2 dumbbell), thickness: 1 mm
Cross head rate: 100 mm/min
Load cell: 20 N
Measurement temperature: 23° C.

[Melt Viscosity (B-type Viscosity)]

According to JIS K6862 and using a Brookfield rotary viscometer, the melt viscosity was measured at 160° C.

[Coatability]

For evaluation of coatability, the spiral pattern at a coating discharge rate of 3 cc/min or 5 cc/min in producing a bonded test piece was observed as to whether or not the pattern could be in a clear circular form and as to how the circular form has deformed. The evaluation criteria are shown in FIG. 1. The case where a circular pattern like in Evaluation A in FIG. 1 was drawn was evaluated as "A", and the case where a deformed pattern like in Evaluation B in FIG. 1 was drawn was evaluated as "B".

TABLE 2

| | Example | | 1 | 2 | 3 | 4 | 5 | 6 | 7 | 8 | 9 |
|---|---|---|---|---|---|---|---|---|---|---|---|
| Base Polymer | Propylenic Polymer (A) | Sample | A3 | A1 | A1 | A2 | A2 | A2 | A3 | A3 | A1 |
| | | Blending Amount (% by mass) | 5 | 18 | 36 | 18 | 35 | 40 | 27 | 25 | 18 |
| | Olefinic Polymer (B) | Sample | B1 | B1 | B1 | B1 | B1 | B1 | B1 | B1 | B2 |
| | | Blending Amount (% by mass) | 95 | 82 | 64 | 82 | 65 | 60 | 73 | 75 | 82 |
| | | Tensile Modulus of Elasticity (MPa) | 25.4 | 25.2 | 34.6 | 35.7 | 59.0 | 61.8 | 62.1 | 65.9 | 20.6 |
| | | Elongation at Break (%) | 190.4 | 417.9 | 564.2 | 271.0 | 486.0 | 381.3 | 312.6 | 390.9 | 63.7 |
| Hot-Melt Adhesive | Base Polymer | (part by mass) | 100 | 100 | 100 | 100 | 100 | 100 | 100 | 100 | 100 |
| | (C) Tackifier Resin | (part by mass) | 55 | 55 | 55 | 55 | 55 | 55 | 55 | 55 | 55 |
| | (D) Oil | (part by mass) | 27 | 27 | 27 | 27 | 27 | 27 | 27 | 27 | 27 |
| | Melt Viscosity (160° C.)(mPa·s) | | 2900 | 3100 | 3200 | 3300 | 3100 | 3100 | 3200 | 3400 | 4800 |
| | Tensile Modulus of Elasticity (MPa) | | 1.4 | 1.8 | 2.6 | 2.5 | 3.9 | 4.7 | 5.8 | 3.9 | 2.8 |
| Evaluation | Adhesive Strength NW/NW (gf) | 3 gsm | 195 | 160 | 189 | 166 | 234 | 269 | 290 | 271 | 127 |
| | | 4 gsm | 252 | 217 | 235 | 266 | 260 | 318 | 357 | 338 | 151 |
| | | 5 gsm | 298 | 254 | 308 | 314 | 338 | 353 | 412 | 379 | 167 |
| | Adhesive Strength PE/NW (gf) | 3 gsm | 231 | 197 | 229 | 233 | 151 | 123 | 136 | 149 | 123 |
| | | 4 gsm | 234 | 226 | 255 | 247 | 187 | 183 | 153 | 175 | 157 |
| | | 5 gsm | 256 | 274 | 250 | 258 | 216 | 177 | 176 | 187 | 164 |
| | Semi-crystallization Time | min | 2.2 | 3.3 | 3.8 | 2.5 | 2.2 | 2.2 | 1.5 | 1.6 | 1.0 |
| | Coatability | | A | A | A | A | A | A | A | A | A |

TABLE 3

|  |  |  | Comparative Example | 1 | 2 | 3 | 4 |
|---|---|---|---|---|---|---|---|
| Base Polymer | Propylenic Polymer (A) | Sample | | A1 | — | A1 | A3 |
|  |  | Blending Amount (% by mass) | | 63 | 0 | 73 | 82 |
|  | Olefinic Polymer (B) | Sample | | B1 | B1 | B1 | B2 |
|  |  | Blending Amount (% by mass) | | 37 | 100 | 27 | 18 |
|  | Tensile Modulus of Elasticity (MPa) | | | 50 | 15.3 | 61.2 | 455.2 |
|  | Elongation at Break (%) | | | 693.9 | 342.2 | 661.5 | 495.9 |
| Hot-Melt Adhesive | Base Polymer | (part by mass) | | 100 | 100 | 100 | 100 |
|  | (C) Tackifier Resin | (part by mass) | | 55 | 55 | 55 | 55 |
|  | (D) Oil | (part by mass) | | 27 | 27 | 27 | 27 |
|  | Melt Viscosity (160° C.)(mPa · s) | | | 3500 | 3200 | 3500 | 4100 |
|  | Tensile Modulus of Elasticity (MPa) | | | 5.3 | 0.9 | 6.1 | 56.1 |
| Evaluation | Adhesive Strength NW/NW (gf) | 3 gsm | | 289 | 186 | 306 | 122 |
|  |  | 4 gsm | | 352 | 209 | 319 | 140 |
|  |  | 5 gsm | | 395 | 241 | 467 | 62 |
|  | Adhesive Strength PE/NW (gf) | 3 gsm | | 116 | 220 | 98 | 7 |
|  |  | 4 gsm | | 133 | 239 | 100 | 9 |
|  |  | 5 gsm | | 145 | 250 | 120 | 15 |
|  | Semi-crystallization Time | min | | 5.5 | 2.7 | 6.2 | 1.9 |
|  | Coatability | | | A | B | A | A |

INDUSTRIAL APPLICABILITY

The base polymer of the present invention is excellent in coatability and exhibits a high adhesive strength for bonding PP nonwoven fabrics together, and further exhibits a high adhesive strength for bonding PE film-PP nonwoven fabric, and therefore can be used, for example, for a hot-melt adhesive.

The invention claimed is:

1. A base polymer for hot-melt adhesive, comprising:
   a propylenic polymer (A) having a tensile modulus of elasticity at 23° C. of 60MPa or more, and
   an olefinic polymer (B) having a tensile modulus of elasticity at 23° C. of less than 60 MPa, wherein:
   relative to 100 parts by mass of the total amount of the propylenic polymer (A) and the olefinic polymer (B), the content of the propylenic polymer (A) is 1 part by mass or more and less than 50 parts by mass, and the content of the olefinic polymer (B) is more than 50 parts by mass and 99 parts by mass or less, wherein weight-average molecular weight (Mw) of the propylenic polymer (A) is 10,000 to 52,000.

2. The base polymer for hot-melt adhesive according to claim 1, wherein the content of the propylenic polymer (A) is 1 part by mass or more and 40 parts by mass or less, and the content of the olefinic polymer (B) is 60 parts by mass or more and 99 parts by mass or less.

3. The base polymer for hot-melt adhesive according to claim 1, wherein the propylenic polymer (A) is a propylene homopolymer.

4. The base polymer for hot-melt adhesive according to claim 1, wherein the tensile modulus of elasticity at 23° C. of the propylenic polymer (A) is 90 MPa or more.

5. The base polymer for hot-melt adhesive according to claim 1, wherein the olefinic polymer (B) is a copolymer of at least two selected from the group consisting of propylene, ethylene and α-olefins each having 4 to 24 carbon atoms, a propylene homopolymer, or an ethylene homopolymer.

6. The base polymer for hot-melt adhesive according to claim 1, wherein the olefinic polymer (B) is a copolymer of propylene, ethylene and 1-butene.

7. The base polymer for hot-melt adhesive according to claim 1, wherein the propylenic polymer (A) has a melting point of 120° C. or lower.

8. The base polymer for hot-melt adhesive according to claim 1, wherein the olefinic polymer (B) has a melting point of 50° C. or higher and 160° C. or lower.

9. A hot-melt adhesive, comprising:
   a base polymer for hot-melt adhesive according to claim 1; and
   at least one selected from the group consisting of (C) a tackifier resin and (D) an oil.

10. The hot-melt adhesive according to claim 9, which satisfies the following (1) and (2):
    (1) the tensile modulus of elasticity at 23° C. of the base polymer is 400 MPa or less; and
    (2) the semi-crystallization time at 25° C. of the hot-melt adhesive is 5 minutes or less.

11. A method of bonding a substrate to another substrate, the method comprising
    melting a hot-melt adhesive according to claim 9, and applying the melted hot-melt adhesive to at least one substrate; and
    bonding another substrate to the applied hot-melt adhesive.

12. A sanitary article, comprising a hot-melt adhesive according to claim 9.

* * * * *